US00PP29963P2

(12) United States Plant Patent
Cain

(10) Patent No.: US PP29,963 P2
(45) Date of Patent: Dec. 11, 2018

(54) GRAPEVINE PLANT NAMED 'IFG TWENTY-SEVEN'

(50) Latin Name: ***Vitis interspecific* hybrid**
Varietal Denomination: IFG Twenty-seven

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/731,718

(22) Filed: Jul. 24, 2017

(51) Int. Cl.
*A01H 5/08* (2018.01)

(52) U.S. Cl.
USPC ..... Plt./205
CPC ..... *A01H 5/08* (2013.01)

(58) Field of Classification Search
USPC ..... Plt./205
CPC ..... A01H 5/0812
See application file for complete search history.

*Primary Examiner* — Kent L Bell

(57) ABSTRACT

This invention is a new and distinct grapevine variety denominated 'IFG Twenty-seven'. The new grapevine is characterized by producing crisp red berries having a cylindrical shape with a strong fruity labrusca flavor. Fruits normally ripen late July to early August near Delano Calif.

1 Drawing Sheet

Latin name of the genus and species claimed: *Vitis interspecific* hybrid.

Variety denomination: 'IFG Twenty-seven'.

BACKGROUND OF THE INVENTION

The new and distinct grapevine plant described and claimed herein originated from a hand pollinated cross of the 'Princess' variety (non-patented), and A2798 (unnamed interspecific) hybridized in May 2005. The abortive seed traces were subsequently embryo cultured and the resulting population of plants was planted in the field in April 2006. The present variety of grapevine was selected as a single plant in October 2008 and was first asexually propagated by hardwood cuttings in December 2008 near Delano, Kern County, Calif. The resulting propagules were planted during April 2009 near Delano, Kern County, Calif. and were found to reproduce true-to-type through at least two generations of asexual reproduction.

BRIEF SUMMARY OF THE INVENTION

The new grapevine 'IFG Twenty-seven' is characterized by producing crisp red berries having a cylindrical shape with a strong fruity labrusca flavor. Fruits normally ripen late July to early August near Delano Calif. Fruits are fairly low in acidity, with medium dense, firm, crisp texture. Attachment of the berry to the pedicel is somewhat weak. Vines are vigorous, very productive and can be pruned to short spurs.

The new grapevine differs from its maternal parent the 'Princess' variety by having red rather than green berries and by having a very strong fruity labrusca type flavor as opposed to the neutral to faint muscat flavor of 'Princess'. The berries of 'IFG Twenty-seven' are more elongated than the 'Princess' variety and the peduncle is weaker and less lignified. 'IFG Twenty-seven' can be distinguished from its pollen parent, A2798, by having a smaller, more elongated and less firm berry and by having red rather than black berries.

Grape breeders have used several native American grape species to improve hardiness, disease and insect resistance as well as incorporate aromatic flavors into the vinifera species. Previously introduced interspecific varieties have had very limited commercial success due to small fruit size, large seed traces, slip-skin texture or lack of firmness. The new grapevine variety is being introduced because of its unique combination of labrusca flavor combined with firm texture, seedlessness, good adhesion of skin and flesh and naturally medium large berry size.

BRIEF DESCRIPTION OF THE DRAWING

The accompanying photographic drawing in FIG. 1 illustrates in full color 'IFG Twenty-seven', taken from a 6-year-old vine. The photograph was taken outdoors with indirect lighting. The colors are as nearly true as is reasonably possible in a color representation of this type. The left side of the drawing has mature leaves. A mature fruit cluster is represented in the center of the drawing along with a typical berry in cross section. A young shoot tip with tendrils can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2015 by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Twenty-seven' plants grown in the vicinity of Delano, Kern County, Calif. during 2015 to 2017, and is believed to apply to plants of the variety grown under similar conditions of soil and climate elsewhere:

VINE

General:
- *Vigor*.—Vigorous.
- *Density of foliage*.—Dense.
- *Productivity*.—Very productive, producing about 43 to 65 kg of fruit per vine.
- *Root stock*.—Own root.
- *Training method*.—Typically spur pruned leaving 2 bud spurs.

Trunk:
- *Trunk diameter of 6-year-old vines at 30 cm above the soil line*.—About 9.0 cm.
- *Straps*.—Long — continuous.
- *Surface texture*.—Medium rough texture.
- *Inner bark color*.—The following colors were observed: Greyed-orange: 166A and 166B.
- *Outer bark color*.—Grey-brown: N199B.

SHOOTS

Young shoot:
- *Form of tip*.—Wide open.
- *Distribution of anthocyanin coloration of tip*.—Absent or very weak overall.
- *Intensity and color of anthocyanin coloration of tip*.—Very weak: Red-purple: 59B.
- *Density of prostrate hairs of tip*.—Medium.
- *Density of erect hairs on tip*.—Absent.
- *Color*.—Yellow-green: 144A.

Woody shoot (mature canes):
- *Internode length*.—Medium: About 7.7 cm.
- *Width at node*.—About 1.4 cm.
- *Cross section*.—Circular to slightly elliptic.
- *Surface*.—Striate.
- *Main color*.—The following colors were observed: Greyed-orange: 166A and 166B and 166C and 166D.
- *Density of erect hairs on nodes*.—None.
- *Density of erect hairs on internodes*.—None.
- *Axillary shoot length at full bloom*.—Medium: Approximately 10.3 cm.

Flowering shoot:
- *Vigor during flowering*.—Strong.
- *Attitude during flowering on shoots not tied*.—Erect.
- *Color*.—Dorsal side of internodes — Yellow-green: 146C, with Red-purple stripes: 59B.
- *Color*.—Ventral side of internodes — Yellow-green: 146C, with Red-purple stripes: 59B.
- *Color*.—Dorsal side of nodes — Yellow-green: 146C, with Red-purple stripes: 59B.
- *Color*.—Ventral side of nodes — Yellow-green: 146C.
- *Density of prostrate hairs on nodes*.—Sparse.
- *Density of erect hairs on nodes*.—None.
- *Density of prostrate hairs on internode*.—Very sparse.
- *Density of erect hairs on internode*.—None.
- *Anthocyanin coloration of buds*.—Absent.

Tendrils:
- *Distribution on the shoot (at full flowering)*.—Discontinuous.
- *Length of tendril*.—Long: About 27.1 cm.
- *Thickness of tendril 2 cm from base*.—About 3.0 mm.
- *Color*.—Yellow-green: 146C.
- *Form*.—Bifurcated and trifurcated.
- *Number of consecutive tendrils*.—2.

LEAVES

Young leaves:
- *Color of upper surface of first four distal unfolded leaves*.—Yellow-green: 144A.
- *Color of lower surface of young leaves*.—Yellow-green: 144A.
- *Average intensity of anthocyanin coloration of six distal leaves prior to flowering*.—Absent.
- *Density of prostrate hairs between veins (lower surface)*.—Very sparse.
- *Density of prostrate hairs on veins (lower surface)*.—Very sparse.
- *Density of erect hairs between veins (lower surface)*.—Sparse to medium.
- *Density of erect hairs on veins (lower surface)*.—Medium.

Mature leaves (opposite first cluster):
- *Average length*.—About 13.8 cm.
- *Average width*.—About 19.2 cm.
- *Mature leaf size*.—Medium large.
- *Shape of blade*.—Wedge-shaped.
- *Number of lobes*.—5.
- *Blade venation*.—Palmate.
- *Vein color*.—Yellow-green: 145C.
- *Anthocyanin coloration of main veins on upper side of blade*.—Absent.
- *Mature leaf profile*.—Flat.
- *Blistering surface of blade upper surface*.—Weak to medium.
- *Leaf apex*.—Accute.
- *Leaf blade tip*.—In the plane of the leaf.
- *Leaf margin*.—Serrate.
- *Undulation of margin*.—Slight.
- *Undulation of blade between main and lateral veins*.—Absent.
- *Shape of teeth*.—Both sides concave.
- *Length of teeth*.—Very short.
- *Ratio length/width of teeth*.—Small.
- *Shape of upper lateral sinuses*.—Open.
- *Depth of upper lateral sinuses*.—Shallow.
- *General shape petiole sinus*.—Slightly open.
- *Shape of base of upper leaf sinuses*.—V-shaped.
- *Tooth at petiole sinus*.—Absent.
- *Density of prostrate hairs between veins on lower surface of blade*.—Absent.
- *Density of erect hairs between veins on lower surface of blade*.—Sparse.
- *Density of prostrate hairs on main veins on lower surface of blade*.—Very sparse.
- *Density of erect hairs on main veins on lower surface of blade*.—Medium dense.
- *Density of prostrate hairs on main veins on upper surface of blade*.—Very sparse.
- *Density of erect hairs on main veins on upper surface of blade*.—None.

*Autumn coloration of leaves*.—Leaves can be a single color or combination of colors, in a mottled pattern or on the edges of the leaves. The following colors were observed: Greyed-yellow: 162A and 162B and Greyed-purple: 187A and 184A and Greyed-red: 181A and 181B.

Upper surface:

*Color*.—Green: 137A.

*Anthocyanin coloration of main veins* (*lower surface*).—Absent.

*Surface appearance*.—Semi-glossy.

*Blistering surface of blade*.—Weak.

Lower surface:

*Color*.—Yellow-green: 146B.

*Anthocyanin coloration of main veins* (*lower surface*).—Absent.

*Glossiness*.—Weak.

*Surface texture*.—Smooth.

*Surface appearance*.—Dull.

Petiole:

*Length*.—About 12.2 cm.

*Diameter of petiole* 2 *cm from blade*.—About 3.9 mm.

*Petiole color*.—The following colors were observed: Yellow-green: 145B and 145C.

*Length of petiole compared to middle vein*.—Slightly shorter.

*Density of prostrate hairs on petiole*.—None.

*Density of erect hairs on petiole*.—Sparse.

Buds:

*Bud fruitfulness*.—Basal: mostly fruitful.

*Position of first fruitful shoot on previous season cane*.—$1^{st}$ to $2^{nd}$ node.

*Dormant bud length*.—About 5.8 mm.

*Dormant bud width in the proximal/distal plane*.—About 6.4 mm.

*Dormant bud color*.—Greyed-orange: 166A.

*Time of bud burst*.—Midseason: About Mar. 5, 2016.

FLOWERS

General:

*Flower sex*.—Hermaphrodite.

*Length of single flower, unopened*.—About 2.9 mm.

*Width of single flower*.—Unopend: About 1.8 mm, opened: About 4.6 mm.

*Stamen length*.—2.5 mm.

*Stamen count*.—5, few with 6.

*Pollen color*.—Yellow: 10A.

*Pistil length*.—About 2.1 mm.

*Pistil color*.—Yellow-green: 144A.

*Length of first inflorescence*.—Medium: About 18.0 cm long by 14.5 cm wide.

*Position of first flowering and fruiting node*.—$3^{rd}$ to $4^{th}$ node (current season growth).

*Number of inflorescence per flowering shoot*.—1.1 to 2: About 1.9

*Time of bloom*.—Late as compared with similar varieties in the growing area of Delano, Calif.

*Date of full bloom*.—About May 9, 2017.

FRUIT

General:

*Ripening period*.—Midseason: Approximately Aug. 7, 2015.

*Use*.—Fresh market.

*Keeping quality*.—Average, remains commercially acceptable when stored up to 6 weeks at 0° C. and high Relative Humidity.

*Resistance to*.—Insects: Average typical of *Vitis vinifera* species. Diseases: Average typical of *Vitis vinifera* species.

*Refractometer test*.—Soluble solids: About 23.0 Brix.

*Brix/acid*.—About 32.4.

*Titratable acidity*.—About 0.71.

*Juice ph*.—About 3.72.

Cluster:

*Mature cluster length* (*peduncle excluded*).—About 21.1 cm.

*Mature cluster width*.—About 21.6 cm.

*Mature cluster weight*.—About 1448 g.

*Bunch density*.—Medium.

*Number of berries*.—About 248.

*Form*.—Conical.

Peduncle:

*Lignification of peduncle*.—Weak.

*Width of peduncle*.—About 5.5 mm.

*Length of peduncle*.—Medium: Approximately 4.2 cm.

*Peduncle color*.—Yellow-green: 144C.

Berry:

*Uniformity of size*.—Uniform.

*Single berry weight*.—About 6.6 g.

*Shape*.—Cylindrical.

*Seeds*.—Absent.

*Cross section*.—Circular.

*Berry dimensions*.—Longitudinal axis: About 2.8 cm. Horizontal axis: About 1.9 cm.

*Pedicel length*.—About 7.0 mm.

*Pedicel width*.—About 2.0 mm.

*Pedicel color*.—Yellow-green: 144C.

*Berry firmness*.—Moderate.

*Particular flavor*.—Labrusca.

*Bloom* (*cuticular wax*).—Medium.

*Berry separation from pedicel*.—Somewhat easy.

*Flesh color*.—The following colors were observed: Greyed-white: 156B and 156C.

*Skin color* (*without bloom*).—Greyed-purple: 187B.

Skin:

*Thickness*.—Thin.

*Skin toughness*.—Not notable when chewing.

*Reticulation*.—Absent.

*Tenacity*.—Tenacious to flesh.

What is claimed:

1. A new and distinct variety of grapevine plant as herein illustrated and described.

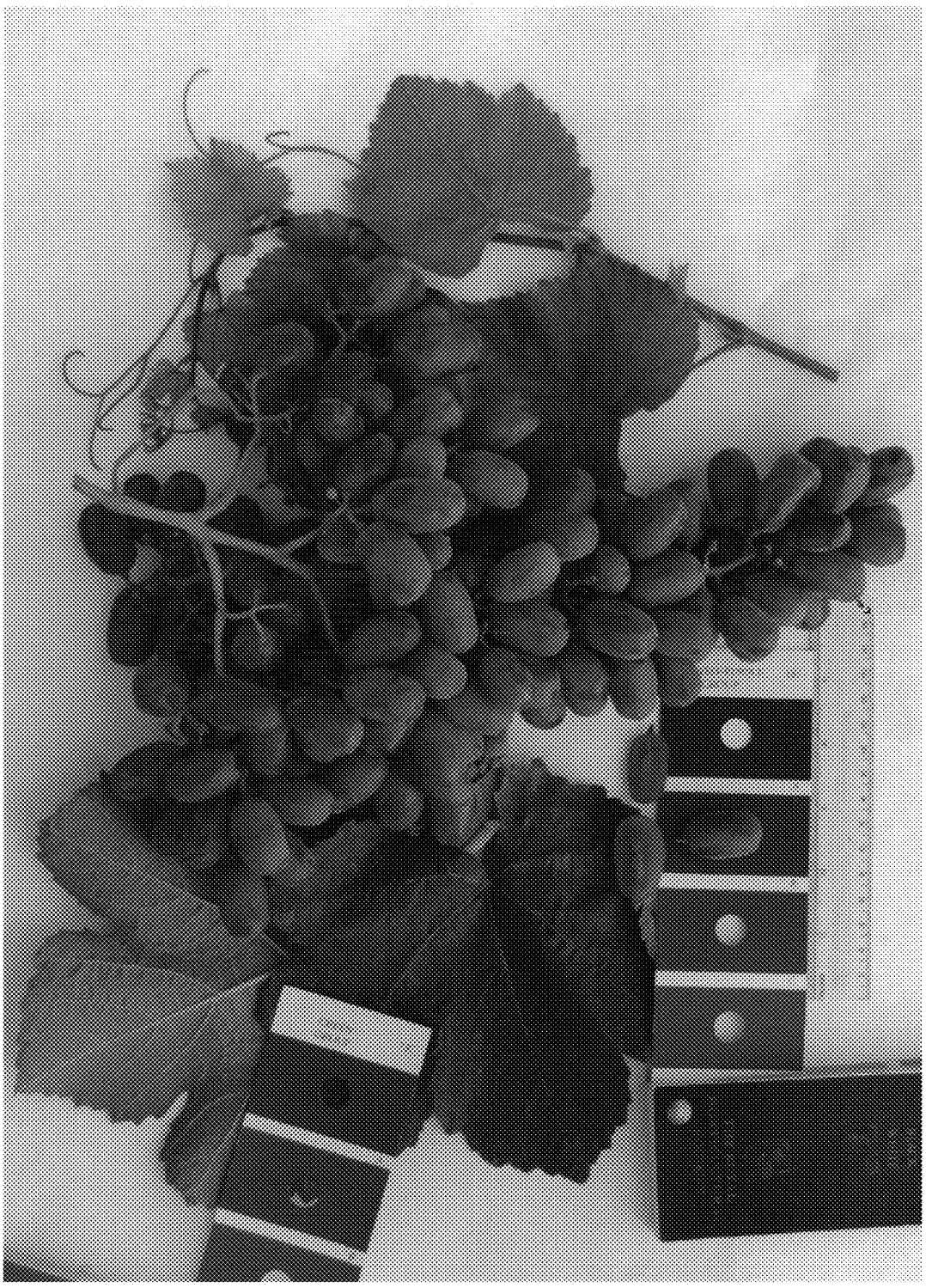

* * * * *